(12) United States Patent
Gulsen et al.

(10) Patent No.: US 12,138,116 B2
(45) Date of Patent: Nov. 12, 2024

(54) INTRALUMINAL MEDICAL IMAGING INTERFACE DEVICES AND SYSTEMS

(71) Applicant: KONINKLIJKE PHILIPS N.V., Eindhoven (NL)

(72) Inventors: Ashen Gulsen, Eindhoven (NL); Volker Barnhart Verschoor, Eindhoven (NL); Andrew Mitchell, Eindhoven (NL); Godefridus Antonius Harks, Rijen (NL); Stephen Charles Davies, El Dorado Hills, CA (US); Dirk Jan Nelly Vananderoye, Bree (BE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 940 days.

(21) Appl. No.: 17/052,222

(22) PCT Filed: Apr. 25, 2019

(86) PCT No.: PCT/EP2019/060566
§ 371 (c)(1),
(2) Date: Nov. 2, 2020

(87) PCT Pub. No.: WO2019/211150
PCT Pub. Date: Nov. 7, 2019

(65) Prior Publication Data
US 2022/0008036 A1    Jan. 13, 2022

Related U.S. Application Data

(60) Provisional application No. 62/665,702, filed on May 2, 2018.

(51) Int. Cl.
*A61B 8/00* (2006.01)
*A61M 25/01* (2006.01)
(Continued)

(52) U.S. Cl.
CPC ........... *A61B 8/4209* (2013.01); *A61M 25/01* (2013.01); *A61M 25/0116* (2013.01);
(Continued)

(58) Field of Classification Search
CPC ............... A61B 8/4209; A61B 8/4218; A61M 2209/082; A61M 25/01; A61M 25/0116; A61M 39/1055; A61M 25/02
See application file for complete search history.

(56) References Cited

U.S. PATENT DOCUMENTS

| | | | |
|---|---|---|---|
| 2008/0009745 A1 | 1/2008 | Hossack | |
| 2008/0167750 A1 | 7/2008 | Stahler | |

(Continued)

FOREIGN PATENT DOCUMENTS

| | | |
|---|---|---|
| WO | 2008097540 A2 | 8/2008 |
| WO | 2018060105 A1 | 4/2018 |

(Continued)

OTHER PUBLICATIONS

International Search Report & Written Opinion of PCT/EP2019/060566, dated Jun. 28, 2019.

*Primary Examiner* — Deanna K Hall (57) ABSTRACT

An intraluminal medical imaging interface device includes an arm assembly comprising one or more longitudinal members and one or more joints coupled to the one or more longitudinal members, and a head assembly coupled to a distal portion of the arm assembly and comprising a proximal portion coupled to the distal portion of the arm assembly and a distal portion. The distal portion of the head assembly includes a mechanical coupling and an electrical coupling configured to separably connect to an intraluminal imaging catheter and to transmit electrical signals between a console and the intraluminal imaging catheter. The arm assembly is configured to couple to a surface to maintain the head assembly at a first position and an orientation with respect to (Continued)

a patient without continued support by an operator. Associated devices, systems, and methods are also provided.

20 Claims, 6 Drawing Sheets

(51) Int. Cl.
    *A61M 25/02*     (2006.01)
    *A61M 39/10*     (2006.01)
    *A61B 8/12*     (2006.01)
    *A61M 5/158*     (2006.01)

(52) U.S. Cl.
    CPC ........ *A61M 25/02* (2013.01); *A61M 39/1055* (2013.01); *A61B 8/12* (2013.01); *A61M 2005/1586* (2013.01); *A61M 2205/3561* (2013.01); *A61M 2209/01* (2013.01); *A61M 2209/082* (2013.01)

(56) References Cited

U.S. PATENT DOCUMENTS

| | | |
|---|---|---|
| 2009/0137952 A1* | 5/2009 | Ramamurthy ........... A61B 5/06 604/95.01 |
| 2010/0121138 A1 | 5/2010 | Goldenberg |
| 2012/0071752 A1 | 3/2012 | Sewell |
| 2014/0148759 A1 | 5/2014 | Macnamara |
| 2014/0316269 A1 | 10/2014 | Zhang |
| 2019/0274658 A1 | 9/2019 | Stigall |
| 2019/0282204 A1 | 9/2019 | Sudol |
| 2019/0307420 A1 | 10/2019 | Minas |
| 2020/0029935 A1 | 1/2020 | Davies |
| 2020/0037991 A1 | 2/2020 | Davidsen |
| 2020/0214670 A1 | 7/2020 | Ossmann |

FOREIGN PATENT DOCUMENTS

| | | |
|---|---|---|
| WO | 2018060411 A1 | 4/2018 |
| WO | 2018065405 A1 | 4/2018 |

* cited by examiner

INTRALUMINAL MEDICAL IMAGING INTERFACE DEVICES AND SYSTEMS

TECHNICAL FIELD

The present disclosure relates generally to intraluminal medical imaging systems, in particular, to intraluminal medical imaging interface devices and systems comprising articulating arm assemblies and mounts to support medical imaging catheters in an operating environment during an imaging procedure.

BACKGROUND

Diagnostic and therapeutic ultrasound catheters have been designed for use inside many areas of the human body. In the cardiovascular system, two common diagnostic ultrasound methods are intravascular ultrasound (IVUS) and intracardiac echocardiography (ICE). Typically a single rotating transducer or an array of transducer elements is used to transmit ultrasound at the tips of the imaging catheters. The same transducers (or separate transducers) are used to receive echoes from the tissue. A signal generated from the echoes is transferred to a console which allows for the processing, storing, display, and/or manipulation of the ultrasound-related data.

Imaging catheters are typically controlled by an operator at the operating table. The catheter is inserted into a lumen of the patient, such as a blood vessel, and an imaging tip of the catheter is navigated to a site from which to image a region of interest. The catheter can be navigated by maneuvering a handle attached to the catheter, and/or by manipulating one or more movement controls disposed on the handle. When the imaging tip has reached the region of interest, the operator must continue to hold the handle during the procedure to avoid accidentally moving the handle or triggering one of the movement controls on the handle. Placing the handle on the operating table or other surface could also cause undesirable movement of the catheter inside the patient.

Conventional catheters often include a separate patient interface module (PIM) between the handle of the catheter and the console. The PIM may control various mechanical and electrical functions of the imaging catheter, such as ultrasound pulse generation, image processing, and rotation of the transducer within the catheter, as well as electrically isolating the catheter circuitry and the catheter power supplies. However, the PIM also requires space at the operating table, and the operator must find an appropriate surface to place the PIM during the procedure.

SUMMARY

The present disclosure advantageously describes intraluminal medical imaging interface devices and systems that can improve the workflow of an intraluminal medical imaging procedure. For example, an intraluminal medical imaging system can include an articulating arm coupled or mounted to a surface in an operating environment or procedure room (e.g., operating table), and configured to couple to and support a proximal portion of an intraluminal imaging catheter, such as a handle, or a connector of the catheter. The interface device can support and stably maintain the imaging catheter at a position and orientation with respect to a patient without continued intervention of an operator. Such configurations can allow more consistent and stable placement of the imaging catheter during a procedure. In some aspects, the interface device can also allow for multitasking and improved control of an imaging procedure at the operating table. For example, the interface device can include one-handed controls of the imaging catheter, and shortcut controls to console functions.

In one embodiment, an intraluminal medical imaging interface device includes an arm assembly comprising one or more longitudinal members and one or more joints coupled to the one or more longitudinal members, the arm assembly including a proximal portion and a distal portion, and a head assembly coupled to the distal portion of the arm assembly. The head assembly comprises a proximal portion coupled to the distal portion of the arm assembly and a distal portion that includes a mechanical coupling configured to separably connect to an intraluminal imaging catheter, and an electrical coupling configured to separably connect to the intraluminal imaging catheter to transmit electrical signals between a console and the intraluminal imaging catheter. The arm assembly is configured to couple to a surface within a procedure room to maintain the head assembly at a first position and an orientation with respect to a patient such that the intraluminal imaging catheter is held in place without continued support by an operator.

In some embodiments, the first position and the orientation of the head assembly are adjustable by moving the arm assembly. The head assembly can be configured to rotate about an axis defined by a rotatable joint. In some embodiments, the arm assembly is configured to advance the head assembly toward the patient to a second position while maintaining the orientation of the head assembly with respect to the patient. In some aspects, the arm assembly comprises a first rotatable joint, a second rotatable joint distal of the first rotatable joint, a first longitudinal member extending between the first rotatable joint and the second rotatable joint, and a second longitudinal member extending between the first rotatable joint and the second rotatable joint. The head assembly can extend distally of the second rotatable joint. In some aspects, the proximal portion of the head assembly is coupled to the second rotatable joint. In some aspects, the head assembly is configured to articulate with the arm assembly. In some aspects, the arm assembly comprises a telescoping assembly. In some embodiments, the device can further include a mounting brace configured to fixedly couple to an operating table. In other embodiments, the mechanical coupling includes a recess to receive a handle of the intraluminal imaging catheter.

According to another embodiment of the present disclosure, an intraluminal medical imaging system includes an intraluminal imaging catheter and an interface device. The imaging catheter includes a flexible elongate member comprising a distal portion and a proximal portion, the flexible elongate member configured to be positioned within a body lumen of a patient, a handle coupled to the proximal portion of the flexible elongate member, and an intraluminal imaging assembly coupled to the distal portion and configured to obtain imaging data while the flexible elongate member is positioned within the body lumen. The interface device includes an arm assembly comprising one or more longitudinal members coupled to one or more joints and configured to couple to a surface within a procedure room to maintain the handle of the intraluminal imaging catheter at a first position and an orientation with respect to the patient when the handle is coupled to the interface device, and a head assembly coupled to a distal portion of the arm assembly, the head assembly comprising a mechanical coupling and an electrical coupling, the mechanical coupling and electrical coupling disposed at a distal portion of the head assembly and configured to separably couple to the handle of the intraluminal imaging catheter.

In some embodiments, the head assembly includes a first user control configured to activate a control signal transmitted across the electrical coupling to the imaging catheter. In some embodiments, the intraluminal imaging catheter comprises an intracardiac echocardiography (ICE) imaging catheter. In some embodiments, the mechanical coupling comprises a rotational coupling configured to transfer a torque to a rotatable portion of the intraluminal imaging catheter. In other embodiments, the mechanical coupling comprises a recess to receive the handle of the intraluminal imaging catheter. In still other embodiments, the electrical coupling of the head assembly is configured to mate to an electrical coupling of the handle of the intraluminal imaging catheter such that electrical signals can be passed between the handle and the head assembly.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the medical imaging devices and interfaces are described in terms of intracardiac echocardiography (ICE), it is understood that it is not intended to be limited to this application. The system is equally well suited to any application requiring imaging within a confined cavity or body lumen. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Figure 1:
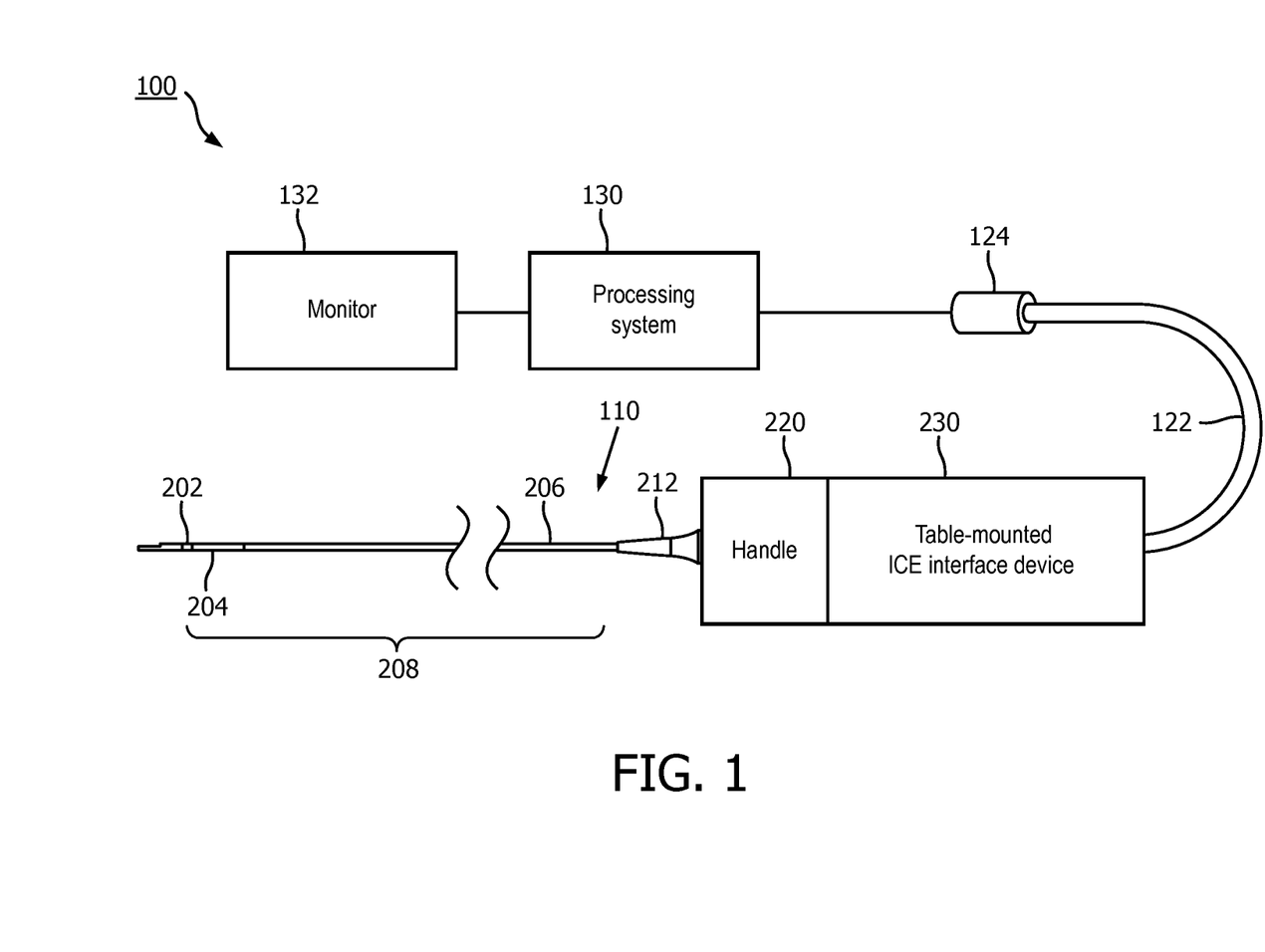
FIG. 1 is a schematic diagram of an ICE imaging system according to embodiments of the present disclosure.

FIG. 1 is a schematic diagram of an ICE imaging system 100 according to embodiments of the present disclosure. The system 100 may include an ICE catheter 110, a connector 124, a processing system 130, such as a console and/or a computer, and a monitor 132. The ICE catheter 110 includes a tip assembly or imaging assembly 202, a flexible elongate member 208, and a handle 220. The flexible elongate member 208 includes a distal portion 204 and a proximal portion 206. The distal end of the distal portion 204 is attached to the tip assembly 202. The proximal end of the proximal portion 206 is attached to the handle 220 for example, by a resilient strain reliever 212, for manipulation and manual control of the ICE catheter 110. The tip assembly 202 can include an imaging core with one or more ultrasound transducer elements (e.g., a transducer array) and associated circuitry. The handle 220 can include actuators clutches, and/or other steering control components for steering the ICE catheter 110, such as deflecting the tip assembly 202 and the distal portion 204, as described in greater detail herein.

Although the present disclosure refers to ICE catheters, any suitable intraluminal imaging device is contemplated, such as an intravascular ultrasound (IVUS) device, an optical coherence tomography (OCT) device, an intracardiac echocardiography (ICE) device, a transesophageal echocardiography (TEE) device, an intravascular photoacoustic (IVPA) imaging device, and/or any suitable internal imaging device. In that regard, the system 100 can be an intraluminal imaging system, and the device 110 can be an intraluminal imaging device (e.g., catheter, guide wire, guide catheter, etc.). For example, the system 100 can be intraluminal ultrasound imaging system, and the device 110 can be an intraluminal ultrasound imaging system. Furthermore, while the following disclosure may refer to intraluminal devices disposed within the vasculature (e.g., blood vessels, arteries, veins, heart chambers, etc.) of a patient, the following disclosure contemplates intraluminal devices sized and shaped, structurally arranged, and/or otherwise configured to be disposed in other internal structures or body lumens of a patient, such as the esophagus, intestines, or other internal structures to be imaged by an intraluminal imaging device. The system 100 may be utilized in a variety of applications such as transseptal lumen punctures, left atrial appendage closures, atrial fibrillation ablation, and valve repairs and can be used to image vessels and structures within a living body. In addition, the tip assembly 202 may include any suitable physiological sensor or component for diagnostics, treatment, and/or therapy.

In the embodiment shown in FIG. 1, the handle 220 is coupled to an interface device 230 which can be coupled to and/or mounted on a surface, such as an operating table, a hospital bed, or any other suitable surface in a medical or surgical environment. In some embodiments, the interface device 230 can comprise an integral unit configured to stably maintain the ICE catheter 110 at a position and orientation with respect to the patient without continued support or intervention by an operator.

The device 230 is in communication with the processing system 130 by the connector 124 and cable 122. By coupling the handle 220 to the device 230, the ICE catheter 110 is in communication with the processing system 130. It will be understood that the handle 220 can also be referred to as a connector in some aspects. In some aspects, the handle 220 can be referred to as an adapter, a coupling, and/or a junction. For instance, in some embodiments, the handle 220 is not held by the operator, but is supported and/or suspended over the operating table and the patient by the device 230. However, for simplicity, the term "handle" is used.

In some embodiments, the system 100 can further include a patient interface module (PIM). For example, the PIM can facilitate communication of signals between the processing system 130 and the ICE catheter 110 to control the operation of the tip assembly 202. This includes generating control signals to configure the imaging assembly 202, generating signals to trigger transmitter circuits, and/or forwarding signals obtained by the tip assembly 202 to the processing system 130. With regard to the echo signals, the PIM can forward the received signals and, in some embodiments, performs preliminary signal processing prior to transmitting the signals to the processing system 130. In examples of such embodiments, the PIM performs amplification, filtering, and/or aggregating of the data. In an embodiment, the PIM also supplies high- and low-voltage DC power to support operation of the circuitry within the tip assembly 202. In some embodiments, the PIM may be included as part of the interface device 230. In that regard, the PIM and the device 230 can comprise a single integral component, in some embodiments. In other embodiments, the PIM may be disposed between the device 230 and the connector 124, or in the handle 220. In other embodiments, such as the embodiment illustrated in FIG. 1, the system 100 may not comprise a PIM.

The connector 124 may be configured in any suitable configuration to interconnect with the processing system 130 and the monitor 132 for processing, storing, analyzing, manipulating, and displaying imaging data obtained from signals generated by the imaging core at the tip assembly 102. The processing system 130 can include one or more processors, memory, one or more input devices, such as keyboards, and/or any suitable command control interface device. The processing system 130 can be operable to facilitate the features of the ICE imaging system 100 described herein. For example, the processing system 130 can execute computer readable instructions stored on the non-transitory tangible computer readable medium. The monitor 132 can be any suitable display device, such as liquid-crystal display (LCD) panel, light emitting diode (LED) panel, or the like.

In operation, a physician or a clinician advances the flexible elongate member 208 into a vessel within a heart anatomy. The physician or clinician can steer the flexible elongate member 208 to a position near the area of interest to be imaged by controlling the handle 220. For example, an actuator on the handle 220 may deflect the tip assembly 202 and the distal portion 204 in a left-right plane and another actuator may deflect the tip assembly 202 and the distal portion 204 in an anterior-posterior plane, as discussed in greater detail herein.

The imaging process may include activating the ultrasound transducer elements on the tip assembly 202 to produce ultrasonic energy. A portion of the ultrasonic energy is reflected by the area of interest and the surrounding anatomy, and the ultrasound echo signals are received by the ultrasound transducer elements. The connector 124 transfers the received echo signals to the processing system 130 where the ultrasound image is reconstructed and displayed on the monitor 132. In some embodiments, the processing system 130 can control the activation of the ultrasound transducer elements and the repletion of the echo signals. In some embodiments, the processing system 130 and the monitor 132 may be part of the same system.

Figure 2:
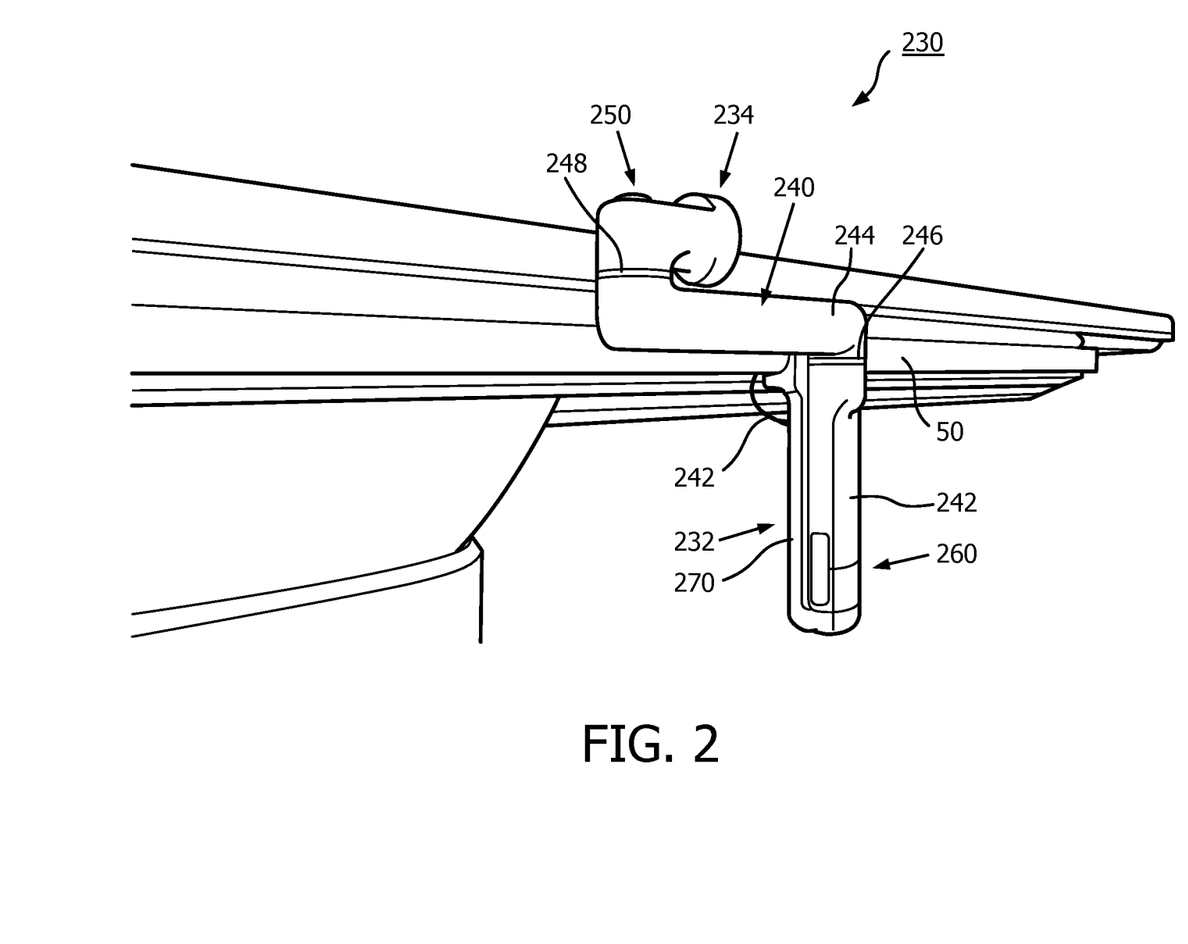
FIG. 2 is a perspective view of an intraluminal imaging interface device coupled to an operating table according to embodiments of the present disclosure.

FIG. 2 depicts the intraluminal medical imaging interface device 230, according to some embodiments of the present disclosure. The device 230 may be included as part of the ICE imaging system 200 shown in FIG. 2. The device 230 is shown coupled to an operating table 50. In some aspects, the device 230 can be mounted, secured, fixed, and/or otherwise coupled to a variety of surfaces, such as the operating table 50, a hospital bed, a rolling table, a counter, or any other suitable surface. The device 230 comprises a proximal portion 332 coupled to the operating table, a distal portion 234, and a plurality of adjustable or maneuverable mechanical components that allow an attached intraluminal imaging device (e.g., 210) to be supported and maintained at a position and/or orientation with respect to a patient. The device 230 can be adjusted to maintain the distal portion 234 at a position and orientation suitable for an intraluminal imaging procedure. For example, in some embodiments, the device 230 can separably couple to a handle 220 of an ICE catheter 210. Before and/or during an imaging procedure, the device 230 can be connected to the handle 220 of the ICE catheter 210 to establish mechanical and/or electrical coupling. After the imaging procedure, the handle 220 can be disconnected from the device 230 in a non-destructive manner. The device 230 can be adjusted or moved to position the ICE catheter 210 near an entry point of the patient, and oriented such that the distal portion 234 of the device 230 faces toward the entry point. The device 230 is configured to maintain the same position and/or orientation of the ICE catheter 210 without continued support or intervention from an operator (e.g., by holding the handle 220).

The device 230 comprises an arm assembly 240 and a head assembly 250. The arm assembly 240 includes a first longitudinal member 242 and a second longitudinal member 244 disposed distal of the first longitudinal member 242. The arm assembly 240 further includes a first joint 246 coupled to and disposed between the first longitudinal member 242 and the second longitudinal member 244, and a second joint 248 coupled to and disposed between the second longitudinal member 244 and the head assembly 250. In other embodiments, the device 230 can comprise fewer or more longitudinal members and/or joints. For example, by increasing the number of longitudinal members and rotatable joints, the device 230 can demonstrate more degrees or modes of movement, potentially allowing for more configurations by an operator. The device 230 may provide for a concertina movement of the head assembly 250 with respect to the operating table 50.

The first and second joints 246, 248 illustrated in FIG. 2 are rotatable joints that facilitate rotation of the first and second longitudinal members 242, 244 and the head assembly 250 with respect to each other. For example, the first joint 246 facilitates rotation of the second longitudinal member 244 about a first axis with respect to the first longitudinal member 242, and vice versa. Because the first longitudinal member 242 is coupled to the operating table 50, rotating the second longitudinal member 244 about the first axis via the first joint 246 can move the second longitudinal member 244 toward and away from the operating table 50. Similarly, the second joint 248 facilitates rotation of the head assembly 250 about a second axis with respect to the second longitudinal member 244.

The arm assembly 240 further comprises a telescoping assembly 260 coupled to the first longitudinal member 242. The telescoping assembly 260 can allow for the arm assembly 240 to extend upwards. By actuating the telescoping assembly 260 to extend upwards, the head assembly 250 can be moved to an elevation appropriate or desired to perform an intraluminal imaging procedure. In the embodiment of FIG. 2, for example, the telescoping assembly 260 facilitates extension of the arm assembly 240 upwards along, or parallel to, the first axis of the first joint 246. In other embodiments, the telescoping assembly 260 facilitates extension of the arm assembly 240 along other axes or directions. The telescoping assembly 260 of FIG. 2 may be referred to as coupled to the first longitudinal member 242. However, in some aspects, the first longitudinal member 242 can be described as comprising the telescoping assembly 260, such that the telescoping assembly 260 allows the first longitudinal member 242 to telescope, or extend, along a direction to increase a length of the first longitudinal member 242. In other embodiments, the telescoping assembly 260 can be included in or coupled to other components of the device 230, such as the first and/or second joint 246, 248. In some embodiments, the telescoping assembly 260 includes a telescoping member slidably received within a lumen of a longitudinal member (e.g., first and/or second longitudinal member 242, 244). The telescoping assembly 260 can also include a locking assembly configured to lock the telescoping member in place to prevent the telescoping member from sliding in one or more directions within the lumen of the longitudinal member. In some embodiments, the telescoping assembly 260 can include more than one telescoping member and/or more than one telescoping assembly at a variety of points along the arm assembly 240 and/or head assembly 250. By increasing the number of telescoping members and/or telescoping assemblies, the device 230 may demonstrate more degrees or modes of freedom, providing an operator with a greater variety of possible positions, orientations, and configurations of the device 230.

The device 230 is mounted to the operating table 50 via a mounting bracket 270 or mounting brace. The mounting bracket 270 is configured to fixedly secure the operating table 50, or any other suitable surface, and to couple to the device 230 to support and/or secure the device 230 to the operating table 50. In some embodiments, the mounting bracket 270 can be part of the device 230, such that the mounting bracket 270 is fixedly attached to the arm assembly 240. In some embodiments, the mounting bracket 270 can be configured to slide along a surface of the operating table 50 while supporting and maintaining the position and/or orientation of the device 230.

Figure 3:
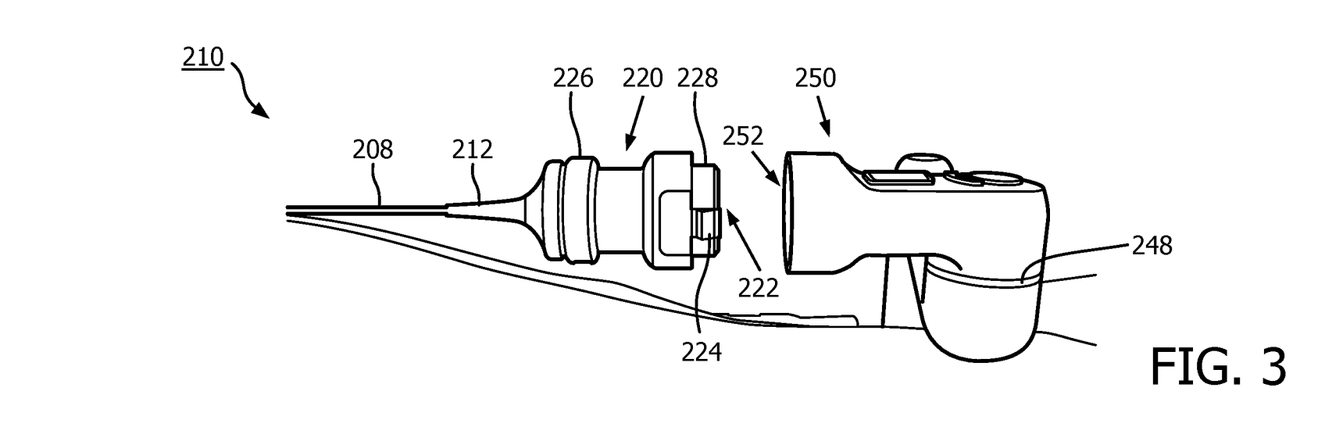
FIG. 3 is a perspective view of an intraluminal imaging interface device and a detached handle of an intraluminal imaging device according to embodiments of the present disclosure.
Figure 4:
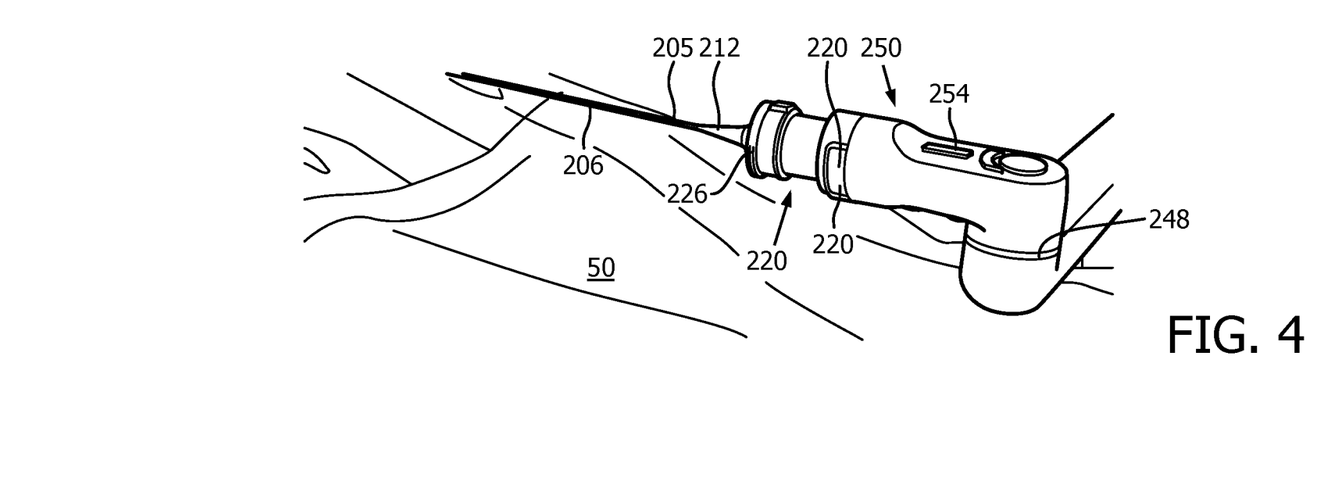
FIG. 4 is a perspective view of an intraluminal imaging interface device and an attached handle of an intraluminal imaging device according to embodiments of the present disclosure.

Referring to FIGS. 3 and 4, the head assembly 250 of the intraluminal imaging interface device 230 is shown with a handle 220 of an ICE catheter 210. The head assembly 250 is coupled to the distal portion 234 of the arm assembly 240. The catheter 210 is configured to be removably coupled to the device 230 via the head assembly 250. In FIG. 3, the handle 220 of the ICE catheter 210 is shown uncoupled from the device 230. The handle 220 is coupled to a proximal portion 206 of a flexible elongate member 208 of the ICE catheter 210 via a strain relief 212. In some embodiments, the flexible elongate member 208 includes one or more pull wires that extend along a length of the device. For example, the flexible elongate member 208 can include one pull wire or a plurality of pull wires extending from the handle 220 to the distal portion of the flexible elongate member 208. The pull wires may be configured to impart movement of the distal portion of the flexible elongate member 208 such as flexion, bending, or deflection. The pull wires may be controlled by one or more controls or inputs of the ICE catheter 210, allowing a user to control movement of the distal portion of the ICE catheter 210 while navigating the ICE catheter 210 through the lumens or other internal structures of the patient. In some embodiments, the controls or inputs that provide control of the pull wires, and thus the distal portion of the flexible elongate member 208, are disposed at the handle 220. However, in other embodiments, the controls may be disposed at other portions of the ICE catheter 210, or may be disposed at other portions of the system 200, such as the interface device 230, processing system 130, and/or the monitor 132.

The ICE catheter 210 extends distally of the handle 220. The head assembly 250 is maintained at a first position and a first orientation with respect to the patient. The head assembly 250 can be moved to a second position and a second orientation by adjusting one or more components of the arm assembly 240 and/or by moving the head assembly 250 relative to the arm assembly 240. For example, the head assembly 250 can be moved to a second orientation by rotating the head assembly 250 relative to the arm assembly 240 via the second joint 248.

The handle 220 of the ICE catheter 210 is configured to be received within a mechanical interface 252 of the head assembly 250. In FIG. 4, the handle 220 is shown coupled to the head assembly 250 of the device 230. A proximal portion 228 of the handle 220 is received within the mechanical interface 252 of the head assembly 250. Now coupled to the head assembly 250, the ICE catheter 210 is also maintained at the first orientation with respect to the patient without continued support and/or intervention by an operator. In this configuration, the head assembly 250 of the device 230 and ICE catheter 210 are sustained and/or suspended above the operating table 50. By sustaining the ICE catheter 210 and head assembly 250 above the operating table 50, the ICE catheter 210 may be stable and less susceptible to unintentional movement of the patient, operator, or operating table 50. As will be discussed below, the device 230 can be configured to control aspects of the ICE catheter 210, such as rotation, extension (advancement), or image capture, while maintaining the head assembly 250 at the first position and/or first orientation.

In some embodiments, the handle 220 of the ICE catheter 210 includes mechanical controls to control movement of the distal portion of the ICE catheter 210. For example, as shown in FIG. 4, the handle 220 can include a ring 226 slidably coupled to an outer surface of the handle 220. The ring 226 may be directly or indirectly coupled to one or more pull wires such that movement of the ring acts on the one or more pull wires to cause movement of the distal portion of the ICE catheter 210. The ring 226 can be coupled to the flexible elongate member 208 such that rotation of the handle 220 rotates the flexible elongate member 208. For instance, translating or retracting the ring 226 proximally toward the head assembly 250 can, via the one or more pull wires, control flexion of the distal portion of the ICE catheter 210, while rotating the ring 226 can rotate the ICE catheter 210. The mechanical controls can be supplemented with rotational controls 254 that control a rotational portion of the ICE catheter 210 to provide degrees of freedom or modes of motion that an operator requires to obtain images of the patient's anatomy. Such a configuration may reduce the number of controls necessary control the distal portion of the ICE catheter 210.

Figure 5:
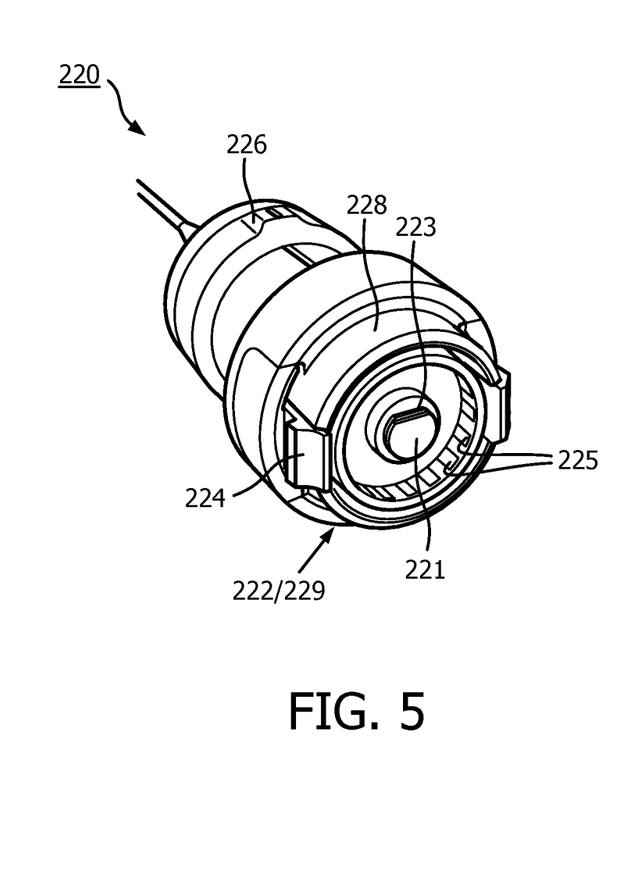
FIG. 5 is a perspective view of a proximal end of a handle of an intraluminal imaging device according to embodiments of the present disclosure.
Figure 6:
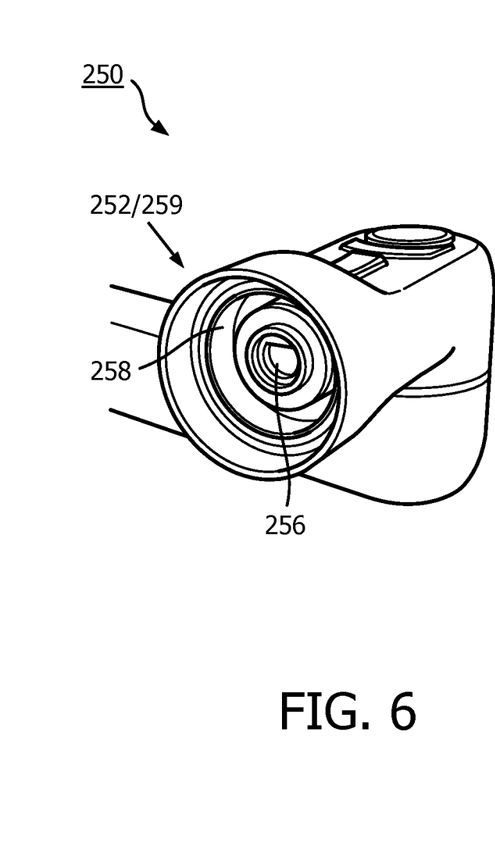
FIG. 6 is a perspective view of a distal end of a head assembly of an intraluminal imaging interface device according to embodiments of the present disclosure.

FIG. 5 depicts a proximal end of a handle 220 of an ICE catheter 210, according to some embodiments. The handle 220 includes a mechanical interface 222 and an electrical interface 229 configured to couple to a mechanical interface 252 and electrical interface 259 of the head assembly 250, shown in FIG. 6. Referring to FIG. 5, the mechanical interface 222 includes a latch connector 224 and a torque transfer member 221. The torque transfer member 221 of the handle 220 shown in FIG. 5 engages a corresponding torque transfer member 256 disposed within the mechanical interface 252 of the head assembly 250 shown in FIG. 6. In some aspects, the torque transfer member 221 of FIG. 5 can be referred to as a male connector, and the torque transfer member 256 of FIG. 6 can be referred to as female. In the illustrated embodiment, the torque transfer member 221 of FIG. 5 includes a cylindrical projection including a flat shelf 223 portion. The torque transfer member 256 of FIG. 6 can include a circular recess having a flat ceiling configured to engage the flat shelf 223 of the torque transfer member 256 of FIG. 5.

In FIG. 5, the handle 220 also comprises an electrical interface 229 disposed within the mechanical interface 222. The electrical interface 229 comprises a plurality of electrical contacts 225 disposed around a circumference of the recess of the mechanical interface 222. In some embodiments, each of the plurality of electrical contacts 225 may provide for electrical communication via a separate communication line. For example, in some embodiments, the electrical interfaces 229, 259 may include 20, 21, or 22 electrical contacts associated with 20, 21, or 22 separate communication lines. In other embodiments, the electrical interface 229 may comprise fewer or more electrical contacts. The electrical contacts 225 of the electrical interface 229 of FIG. 5 can couple to corresponding electrical contacts in the head assembly 250 to establish an electrical communication between the device 230 (and/or the processing system 130) and the ICE catheter 210.

Figure 7:
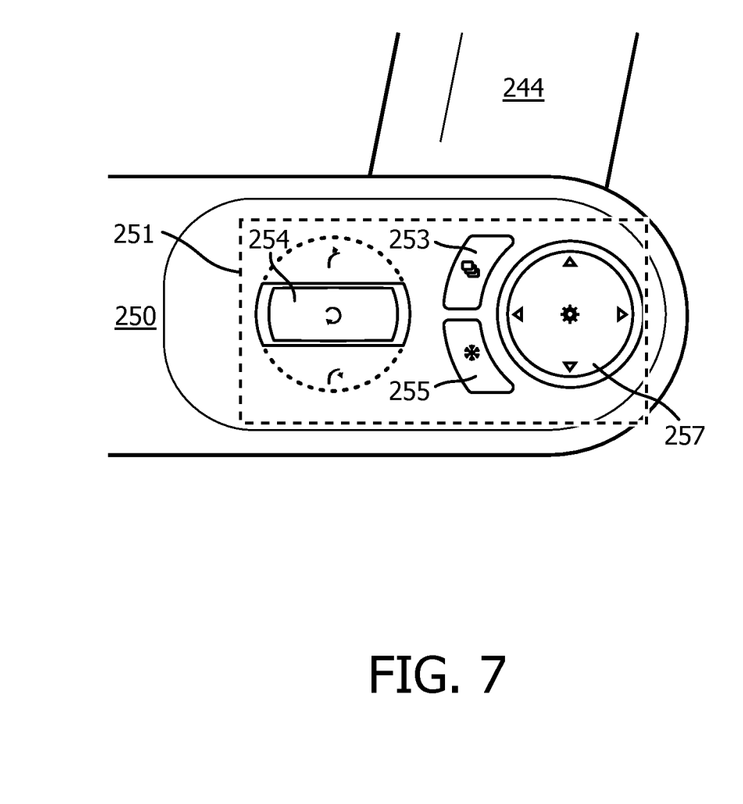
FIG. 7 is a top view of a head assembly of an intraluminal imaging interface device according to embodiments of the present disclosure.

FIG. 7 is a top view of the head assembly 250 shown in FIGS. 1-4 and 6. The head assembly 250 is rotatably coupled to the second longitudinal member 244 via the second joint 248. A controls area 251 disposed on the head assembly 250 includes a plurality of user controls and inputs that allow an operator control various aspects of an intraluminal medical imaging procedure. For example, a rotation control 254 can be twisted, pressed, or otherwise manipulated by the operator to control rotation of a rotatable portion of an imaging device, such as the ICE catheter 210. The rotation control 254 may initiate electrical signals, such as a control signal comprising instructions to activate a rotation mechanism, such as a motor, in the head assembly 250. By activating the rotation mechanism, the torque transfer member 256 of the head assembly 250 can transfer a torque to the torque transfer member 221 of the handle 220 of the ICE catheter 210, which controls rotation of a rotatable portion of the ICE catheter 210. In some embodiments, the rotatable portion of the ICE catheter 210 comprises an elongate drive shaft and an imaging assembly 202 disposed at a distal portion 204 of the drive shaft.

The controls area 251 further includes a first shortcut control 253 and a second shortcut control 255 configured to control aspects of the imaging assembly 202 of the ICE catheter 210. For example, the first shortcut control 253 may initiate an electrical signal comprising instructions for the imaging assembly 202 to capture one or more images, or to perform an imaging sequence or procedure. The second shortcut control 255 may control other aspects of the imaging procedure, such as a freeze function. In some embodiments, the particular functions of the first and second shortcut controls 253, 255 can be set by the operator. For example, the operator may use an operator interface including the monitor 132 to select and/or program the functions carried out by one or more of the shortcut controls 253, 255. The controls area 251 also includes a settings navigation button 257 giving access to additional imaging procedure settings which are adaptive to user preference and procedures requirements. The controls area 251 can include any suitable input device, such as buttons, toggles, switches, etc.

Figure 8:
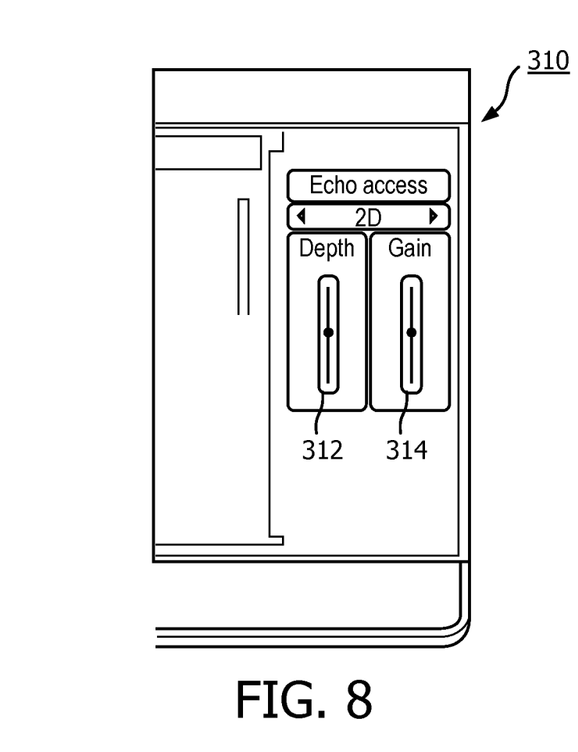
FIG. 8 is an illustration of a portion of a touchscreen interface in communication with an intraluminal imaging interface device according to embodiments of the present disclosure.

FIG. 8 depicts a portion of an operator interface 310 that may be used in conjunction with the controls shown in FIG. 7. The interface 310 can include a first image setting control 312 and a second image setting control 314. In some embodiments, the first and second image setting controls 312, 314 can be used to in conjunction with the shortcut controls 253, 255 shown in FIG. 7. For example, the first and second image setting controls 312, 314 can be used to set image acquisition settings when the first shortcut control 253 is used to acquire an image. In some embodiments, the operator interface 310 comprises a graphical user interface (GUI). The graphical user interface can be used in conjunction with a display and an interface device, such as a mouse and/or a keyboard. In some embodiments, the GUI is used in conjunction with a touch screen display. In some embodiments, the operator interface 310 and/or GUI can be implemented on the head assembly 250, such as a touch screen display. In other embodiments, the operator interface 310 and/or GUI can be implemented on the monitor 132, which is spaced from the interface device 230.

Figure 9:
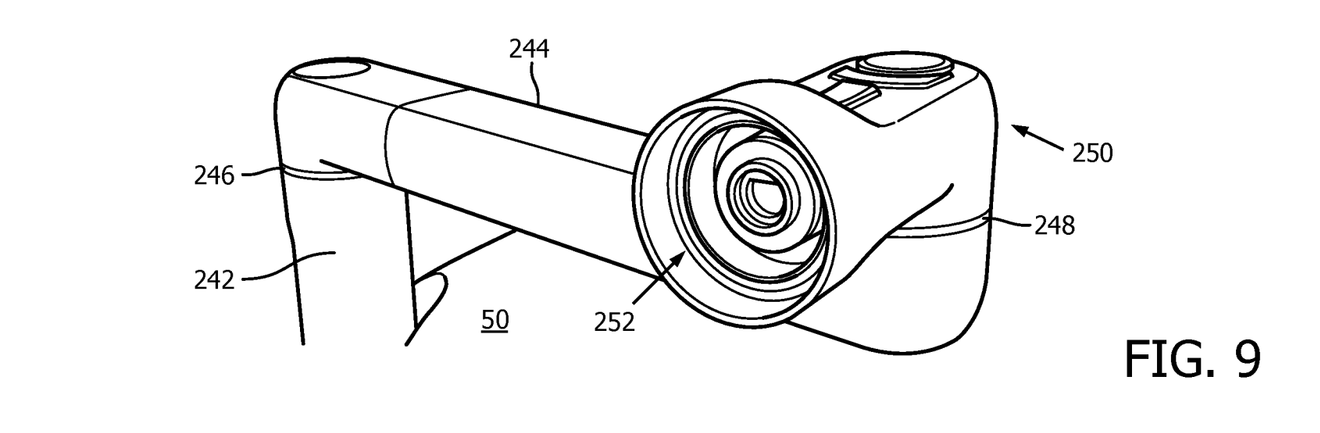
FIG. 9 is a perspective view of an intraluminal imaging interface device according to embodiments of the present disclosure.

FIG. 9 is a perspective view of the intraluminal medical imaging interface device 230 of FIGS. 1-4, 6, and 7, shown with the head assembly 250 suspended above the operating table 50. In some aspects, the device 230 may be telescoped or extended upward with the second longitudinal member 244 rotated over the operating table 50 to support the head assembly 250 over a patient. In some embodiments, the device 230 may be configured and/or intended to remain coupled to the operating table 50 for long periods of time, or even indefinitely, through multiple uses of the device 230. Thus, the device 230 may be considered non-sterile. The ICE catheter 210 that couples to the head assembly 250 can be a disposable device or can be configured for multiple uses. In some instances, because the ICE catheter 210 can be discarded after a single use, the ICE catheter 210, including the handle 220, may be considered sterile. The ICE catheter 210 can also be sterilized between multiple uses and thus be sterile during use.

Figure 10:
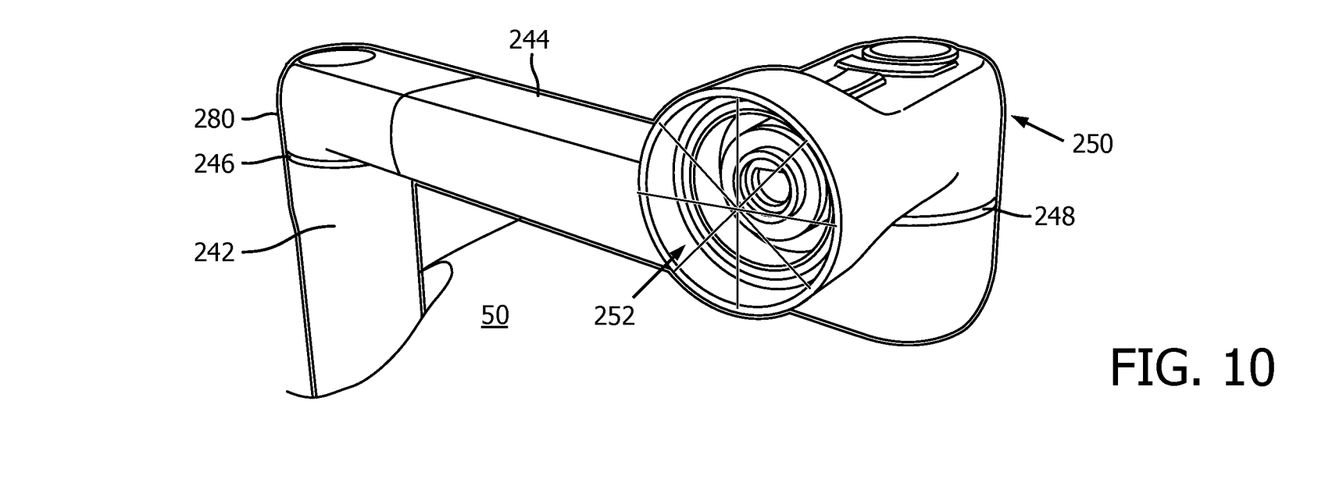
FIG. 10 is a perspective view of an intraluminal imaging interface device covered by a sterile sheath according to embodiments of the present disclosure.

As shown in FIG. 10, in order to maintain the safety and sterility of the operating environment, a sterile sheath 280 is positioned over the device 230 to isolate the non-sterile device 230 from the sterile operating environment. In some embodiments, the sheath 280 can be disposable, e.g., after a single use. In some embodiments, the sheath 280 is initially packaged over the sterile ICE catheter 210. The operator can first couple the handle 220 of the ICE catheter 210 to the head assembly 250 via the mechanical and electrical interfaces 252, 259, and then slide the sheath 280 off of the packaged ICE catheter 210 while simultaneously sliding the sheath 280 over the non-sterile interface device 230. In other embodiments, a new sheath can be placed over the device 230 prior to coupling the handle 220 of the ICE catheter 210 to the head assembly 250 of the device 230.

The devices, systems, and methods described herein can include features similar to those described in, e.g., U.S. Provisional Application No. 62/401,464, filed Sep. 29, 2016, U.S. Provisional Application No. 62/401,686, filed Sep. 29, 2016, U.S. Provisional Application No. 62/401,525, filed Sep. 29, 2016, U.S. Provisional Application No. 62/402,483, filed Sep. 30, 2016, U.S. Provisional Application No. 62/403,431, filed Oct. 3, 2016, U.S. Provisional Application No. 62/403,311, filed Oct. 3, 2016, U.S. Provisional Application No. 62/403,278, filed Oct. 3, 2016, U.S. Provisional Application No. 62/403,267, filed Oct. 3, 2016, U.S. Provisional Application No. 62/468,046, filed Mar. 7, 2017, and U.S. Patent Application Publication No. 2008/0009745, the entireties of which are hereby incorporated by reference herein.

Persons skilled in the art will recognize that the devices, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intraluminal medical imaging interface device, comprising:
    an arm assembly comprising one or more longitudinal members and one or more joints coupled to the one or more longitudinal members, the arm assembly including a proximal portion and a distal portion; and
    a head assembly coupled to the distal portion of the arm assembly, the head assembly and comprising:
        a proximal portion coupled to the distal portion of the arm assembly; and
        a distal portion including:
            a mechanical coupling including a mechanical interface within the head assembly, the mechanical interface of the head assembly configured to separably connect to a mechanical interface of a handle of an intraluminal imaging catheter; and
            an electrical coupling including an electrical interface within the head assembly, the electrical interface of the head assembly configured to separably connect to an electrical interface of the handle of the intraluminal imaging catheter to transmit electrical signals between a console and the intraluminal imaging catheter,
    wherein the arm assembly is configured to removably couple to a surface within a procedure room and to maintain the head assembly at a first position and an orientation with respect to a patient such that the intraluminal imaging catheter is held in place without continued support by an operator.

2. The device of claim 1, wherein the first position and the orientation of the head assembly are adjustable by moving the arm assembly.

3. The device of claim 1, wherein the head assembly is configured to rotate about an axis defined by a rotatable joint.

4. The device of claim 1, wherein the arm assembly is configured to advance the head assembly toward the patient to a second position while maintaining the orientation of the head assembly with respect to the patient.

5. The device of claim 1, wherein the arm assembly comprises:
    a first rotatable joint;
    a second rotatable joint distal of the first rotatable joint;
    a first longitudinal member extending proximal to the first rotatable joint; and
    a second longitudinal member extending between the first rotatable joint and the second rotatable joint,
    wherein the head assembly extends distally of the second rotatable joint.

6. The device of claim 5, wherein the proximal portion of the head assembly is coupled to the second rotatable joint.

7. The device of claim 5, wherein the head assembly is configured to articulate with the arm assembly.

8. The device of claim 5, wherein the arm assembly comprises a telescoping assembly.

9. The device of claim 1, further comprising a mounting brace configured to couple to an operating table.

10. The device of claim 1, wherein the head assembly comprises a recess to receive the handle of the intraluminal imaging catheter.

11. An intraluminal medical imaging system, comprising:
    an intraluminal imaging catheter comprising:
        a flexible elongate member comprising a distal portion and a proximal portion, the flexible elongate member configured to be positioned within a body lumen of a patient;
        a handle coupled to the proximal portion of the flexible elongate member, the handle including a mechanical interface and an electrical interface; and
        an intraluminal imaging assembly coupled to the distal portion and configured to obtain imaging data while the flexible elongate member is positioned within the body lumen; and
    an interface device comprising:
        an arm assembly comprising one or more longitudinal members coupled to one or more joints and configured to removably couple to a surface within a procedure room to maintain the handle of the intraluminal imaging catheter at a first position and an orientation with respect to the patient when the handle is coupled to the interface device; and
        a head assembly coupled to a distal portion of the arm assembly, the head assembly comprising a mechanical coupling including a mechanical interface and an electrical coupling including an electrical interface, the mechanical interface and the electrical interface disposed within a distal portion of the head assembly, the mechanical interface configured to couple to the mechanical interface of the handle of the intraluminal imaging catheter and the electrical interface configured to couple to the electrical interface of the handle of the intraluminal imaging catheter.

12. The system of claim 11, wherein the head assembly comprises a first user control configured to activate a control signal transmitted across the electrical interface to the imaging catheter.

13. The system of claim 11, wherein the intraluminal imaging catheter comprises an intracardiac echocardiography (ICE) imaging catheter.

14. The system of claim 11, wherein the mechanical interface comprises a rotational coupling configured to transfer a torque to a rotatable portion of the intraluminal imaging catheter.

15. The system of claim 11, wherein the head assembly comprises a recess to receive the handle of the intraluminal imaging catheter.

16. The system of claim 11, wherein the electrical interface of the head assembly is configured to mate to an electrical interface of the handle of the intraluminal imaging catheter such that electrical signals can be passed between the handle and the head assembly.

17. The system of claim 11, wherein the flexible elongate member comprises pull wires, and wherein the handle comprises control inputs for the pull wires.

18. The system of claim 11, wherein the mechanical coupling of the head assembly is configured to receive a proximal portion of the handle.

19. The system of claim 11, wherein the mechanical interface coupling of the head assembly comprises a torque transfer member comprising a circular recess having a flat ceiling configured to engage a torque transfer member of the handle.

20. The system of claim 11, wherein the electrical interface of the head assembly is configured to receive electrical contacts of the handle that are disposed around a circumference of a recess within the handle.

\* \* \* \* \*